(12) United States Patent
Cirillo (10) Patent No.: US 11,752,272 B2
(45) Date of Patent: *Sep. 12, 2023

(54) MONITORING DEVICE

(71) Applicant: SHL Medical AG, Zug (CH)

(72) Inventor: William Cirillo, Dublin (IE)

(73) Assignee: SHL MEDICAL AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,120

(22) Filed: Aug. 3, 2022

(65) Prior Publication Data

US 2022/0370724 A1 Nov. 24, 2022

Related U.S. Application Data

(63) Continuation of application No. 16/489,432, filed as application No. PCT/EP2018/054844 on Feb. 27, 2018, now Pat. No. 11,439,764.

(30) Foreign Application Priority Data

Feb. 28, 2017 (EP) .................................... 17158507

(51) Int. Cl.
*A61M 5/31* (2006.01)
*A61M 5/315* (2006.01)

(52) U.S. Cl.
CPC .................. *A61M 5/31568* (2013.01); *A61M 2005/3126* (2013.01); *A61M 2205/3306* (2013.01);
(Continued)

(58) Field of Classification Search
CPC .................. A61M 5/31568; A61M 2005/3126
See application file for complete search history.

(56) References Cited

U.S. PATENT DOCUMENTS

| 9,101,723 B2 | 8/2015 | Larsen |
| 10,773,032 B2 | 9/2020 | Cirillo |

(Continued)

FOREIGN PATENT DOCUMENTS

| CN | 102083489 A | 6/2011 |
| CN | 102740910 A | 10/2012 |

(Continued)

OTHER PUBLICATIONS

Extended European Search Report issued in European Patent Application No. 17158507.8 dated Jun. 23, 2017.

(Continued)

*Primary Examiner* — Courtney B Fredrickson
(74) *Attorney, Agent, or Firm* — McDonnell Boehnen Hulbert & Berghoff LLP (57) ABSTRACT

The present invention relates to a monitoring device (10) arranged to be operably connected to a medicament delivery device (12), said medicament delivery device (12) comprising a manually operated movable dose activation element (20), said monitoring device (10) comprising an electronic circuit (42), said electronic circuit (42) comprising an optical sensor (68), wherein said optical sensor (68) is positioned in relation to said dose activation element (20) so as to detect a manual operation of said dose activation element (20) from an initial position; said electronics circuit further comprising a vibration sensor (70), wherein said vibration sensor (70) is positioned in relation to said medicament delivery device so as to detect specific vibration spectra produced by the medicament delivery device when said dose activating element (20) is operated, wherein said electronic circuit (42) comprises computing elements capable of correlating the information from the optical sensor (68) with the information from the vibration sensor (70) when said dose activation element (20) is operated in order to register when a correct dose has been set.

20 Claims, 8 Drawing Sheets

(52) U.S. Cl.
CPC ............ *A61M 2205/3327* (2013.01); *A61M 2205/3368* (2013.01); *A61M 2205/3375* (2013.01); *A61M 2205/3569* (2013.01); *A61M 2205/3584* (2013.01); *A61M 2205/502* (2013.01); *A61M 2205/505* (2013.01); *A61M 2205/581* (2013.01)

(56) References Cited

U.S. PATENT DOCUMENTS

| | | |
|---|---|---|
| 2008/0051732 A1 | 2/2008 | Chen |
| 2016/0213853 A1 | 7/2016 | Despa |
| 2017/0182258 A1 | 6/2017 | Michael |

FOREIGN PATENT DOCUMENTS

| | | |
|---|---|---|
| EP | 0327910 A2 | 8/1989 |
| WO | 2011117212 A1 | 9/2011 |
| WO | 2014064691 A2 | 5/2014 |
| WO | 2015136513 A1 | 9/2015 |
| WO | 2016071912 A1 | 5/2016 |
| WO | 2016162298 A1 | 10/2016 |
| WO | 2017092960 A1 | 6/2017 |

OTHER PUBLICATIONS

English Translation of Office Action issued in Taiwanese Patent Application No. 107106870 dated Apr. 18, 2019.

Fig. 5

MONITORING DEVICE

CROSS REFERENCE TO RELATED APPLICATIONS

The present application is a continuation of U.S. patent application Ser. No. 16/489,432 filed Aug. 28, 2019, which is a U.S. National Phase Application pursuant to 35 U.S.C. § 371 of International Application No. PCT/EP2018/054844 filed Feb. 27, 2018, which claims priority to European Patent Application No. 17158507.8 filed Feb. 28, 2017. The entire disclosure contents of these applications are herewith incorporated by reference into the present application.

BACKGROUND OF THE INVENTION

There is an ever increased demand for monitoring the handling of medicament delivery devices and in particular medicament delivery devices for self-administration. One important reason for monitoring the handling is to provide a user with information and alerts as to when the next dose delivery is scheduled, based on previous dose deliveries and based on prescribed medication schedules.

Some medicament delivery devices are provided with monitoring units integrated into the medicament delivery device. This has a number of drawbacks. One is that the medicament delivery device becomes rather complicated and expensive to manufacture. This is especially a problem if the medicament delivery device is a so called disposable device that is to be discarded after use. Another drawback is that it is not a simple task to modify a medicament delivery device that already is on the market by integrating monitoring functionality, because such modifications require new approvals from national health authorities before they can be marketed.

An alternative is to provide monitoring units that can be releasably connected to a medicament delivery device. This solution has a number of advantages. First, the monitoring unit may be used many times which is an advantage when disposable medicament delivery devices are used. It is then easy to remove the monitoring unit from a used medicament delivery device that is to be discarded and to connect it to a new medicament delivery device for the subsequent dose delivery. Moreover, the monitoring units may be easily adapted or modified to be connected to medicament delivery devices on the market without the medicament delivery devices being affected regarding design and function by the monitoring units, thereby omitting any intervention by the national health authorities.

One such monitoring unit that may be releasably connected to a medicament delivery device is disclosed in document U.S. Pat. No. 9,101,723. Here an electronics module is attached to an outer surface of a medicament delivery device. The electronics module is arranged with some sort of pressure sensor, alternatively vibration sensor. The electronics module is designed such that the sensor is placed so that it can detect mechanical "click sounds" from engaging parts of the medicament delivery device when e.g. a dose is set and/or delivered.

There are some drawbacks with the design of U.S. Pat. No. 9,101,723. The detected signals from the sensors have to be filtered in order to have only correct signals generated from dose setting and not from signals generated that are not related to the dose setting, for instance if the medicament delivery device is dropped or vibrated in other instances. Even so, it is often difficult to obtain such a filtering function that only detects the correct signals. Further, correct signals may is some instances be "hidden" by other signals that may occur simultaneously, whereby the filtering function may miss the correct signal.

Thus, there is room for improvements related to monitoring units that are connectable to medicament delivery devices.

BRIEF DESCRIPTION OF THE INVENTION

The aim of the monitoring device of this application is to remedy the drawbacks of the state of the art monitoring devices and to provide a monitoring device that can accurately measure and display a set dose.

This aim is obtained by the features of the independent patent claim. Preferable embodiments of the monitoring unit form the subject of the dependent claims.

According to one aspect, a monitoring device is arranged to be operably connected to a medicament delivery device, wherein the medicament delivery device comprises a manually operated movable dose activation element. The monitoring device comprises an electronic circuit, which electronic circuit comprises an optical sensor, wherein the optical sensor is positioned in relation to the dose activation element so as to detect a manual operation of the dose activation element from an initial position.

Further, the electronics circuit comprises a vibration sensor, wherein the vibration sensor is positioned in relation to the medicament delivery device so as to detect specific vibration spectra produced by the medicament delivery device when the dose activating element is operated, wherein the electronic circuit comprises computing elements capable of correlating the information from the optical sensor with the information from the vibration element when the dose activation element is operated in order to register when a correct dose has been set.

Thus, by using both an optical sensor for measuring the movement of the dose activation element and a vibration sensor, a much better measurement accuracy is obtained compared to just using one sensor in that any deviations or tolerance flaws with the medicament delivery device will be compensated by the correlation of the information from both sensors.

According to one aspect the specific vibration spectra is produced by the medicament delivery device at predetermined dose quantity intervals, which typically are pre-configured click sounds produced by components of the medicament delivery device at specific positions of the dose activation element that correspond to specific dose quantities.

Preferably the optical device may be arranged to scan the surface of the movable activating element. Moreover, the vibration sensor may be an accelerometer but can also be a microphone. In addition, the monitoring unit may comprise a user information interface capable of providing information to a user, which may be a display. In this regard, the display may show the dose quantity that has been set, the time and date, status of the power source, the date and time for a subsequent dose if the monitoring unit is provided with such information. Moreover, the monitoring unit may comprise a touch sensor. The touch sensor may be operably connected to the electronic circuit such that the electronic circuit is activated when the touch sensor detects a touch or a movement of the monitoring unit.

The monitoring unit may further comprise at least one communication circuit designed and arranged to communicate with external communication elements. In this regard, the communication circuits may comprise near range communication technology. This enables communication with for instance smart devices such that information may be transferred between the monitoring unit and the smart device. The communication units of the smart devices, such as wifi-circuits or radio frequency communication circuits, may then be used for sending the information obtained by the monitoring unit further to data handling centres on the internet.

In addition or as an alternative, the communication circuits of the monitoring unit may comprise wireless local area network communication technology and/or digital cellular network communication technology. If so then the monitoring unit may communicate directly with data handling centres on the internet and does not require an extra device such as a smart device in order to communicate.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
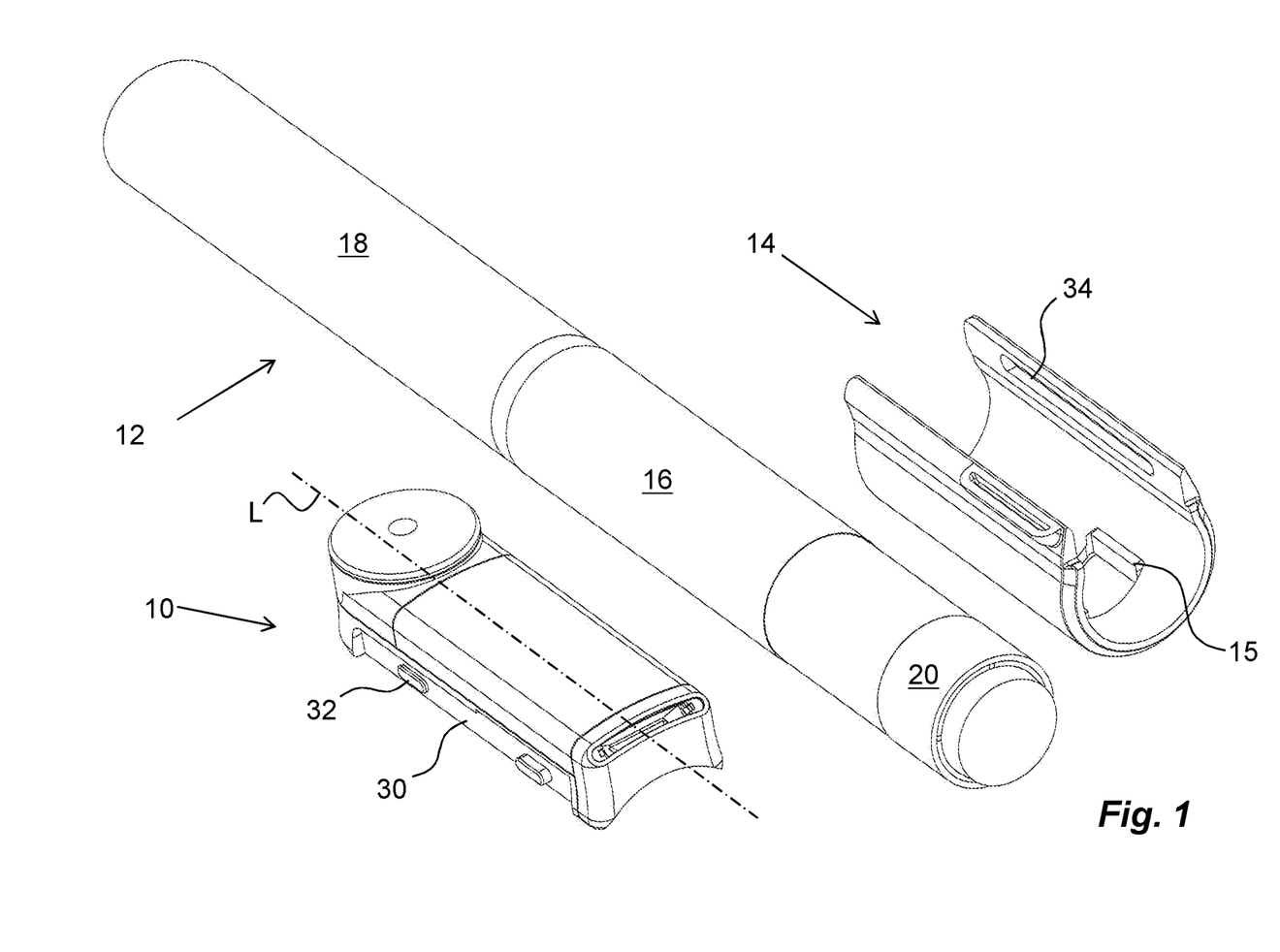
FIG. 1 shows a medicament delivery device and a monitoring unit to be attached to the medicament delivery device with an attachment.

The present invention relates to a smart monitoring device or unit 10 for monitoring the use of medicament delivery devices 12 such as insulin pens as seen in FIG. 1 even though it should be understood that a number of different medicaments may be delivered by the medicament delivery device. The monitoring unit 10 may be connected to the medicament delivery device 12 by suitable connecting elements. FIG. 1 shows one example of a connecting element in the form of an annular sleeve 14 that is designed to be removably mounted on the outside of the medicament delivery device in a secure way. In this regard, the sleeve 14 is preferably adapted to the outer shape and dimensions of the medicament delivery device it is intended to be connected to as well as mechanical fixation elements 15 such as protrusions and/or ledges that are to cooperate with corresponding support surfaces on the medicament delivery device such as side surfaces around an opening or a window for e.g. a dose counter display.

The type of medicament delivery device that the monitoring unit is intended to be connected to comprises a generally elongated tubular housing body 16. The housing body is arranged to accommodate a medicament container, wherein the medicament container is provided with a medicament delivery member such as an injection needle. The medicament delivery member could either be an integral part of the medicament container or be attachable to the proximal part of the medicament container via suitable attachment elements such as threads, bayonet connections, luer connections etc. At the proximal end of the body a protective cap 18 may be releasably attached for protecting the medicament delivery member before use.

Further, a dose activation element 20 is provided. The dose activation element 20 may be provided with a distal grip part 22, which grip part 22 is arranged with a tubular extension 24 wherein the extension is provided with threads 26 so that when the grip part 22 is turned, the dose activation element 20 is extended out of the distal end of the medicament delivery device. When a subsequent dose is to be delivered, the distal end 28 of the grip part 22 is pressed in the proximal direction by a user, whereby the dose activation element 20 is rotated back into the housing of the medicament delivery device, wherein the dose activation element 20 is operably connected to a plunger rod, which in turn acts on a stopper of a medicament container for expelling a dose of medicament. The latter components of the medicament delivery device described above are not shown in the drawings but are inherently present in all medicament delivery devices of the described kind.

The monitoring unit 10 according to the embodiment shown is intended to be connected to a conventional medicament delivery device. The monitoring unit 10 comprises a generally rectangular housing 30, FIGS. 1 and 2. The outer side surfaces of the housing 30 are arranged with attachment elements 32 that are to interact with corresponding attachment elements 34 of the sleeve 14. In the embodiment shown in the drawings, the attachment elements 32 of the monitoring unit 10 comprises outwardly directed protrusions, which are designed to fit into longitudinally extending grooves 34 on oppositely directed inner surfaces of the sleeve 14. It is however to be understood that other types of attachment elements may be utilised in order to provide a positive and firm attachment of the monitoring unit. For example, if the orientation of the monitoring unit in relation to the fastening element and the medicament delivery device is important, a proximal area of the monitoring unit may be arranged with protrusions in one end of the housing and recesses in the other end of the housing and that the fastening element comprises complementary attachment elements so that the monitoring unit may only be attached to the fastening element in one direction. The lower part of the housing 30, which is directed towards a medicament delivery device when fastened, is somewhat curved or concave to follow the curvature of the medicament delivery device. The monitoring unit is further arranged with an end piece 36 that is attachable to an end surface of the housing. A lower surface 38 of the end piece has the same curvature as the lower part of the housing 30, FIG. 2. The lower part of the housing 30 is provided with a passage 40, which passage 40 is intended for sensors on the monitoring unit, the function of which will be described below.

Figure 2:
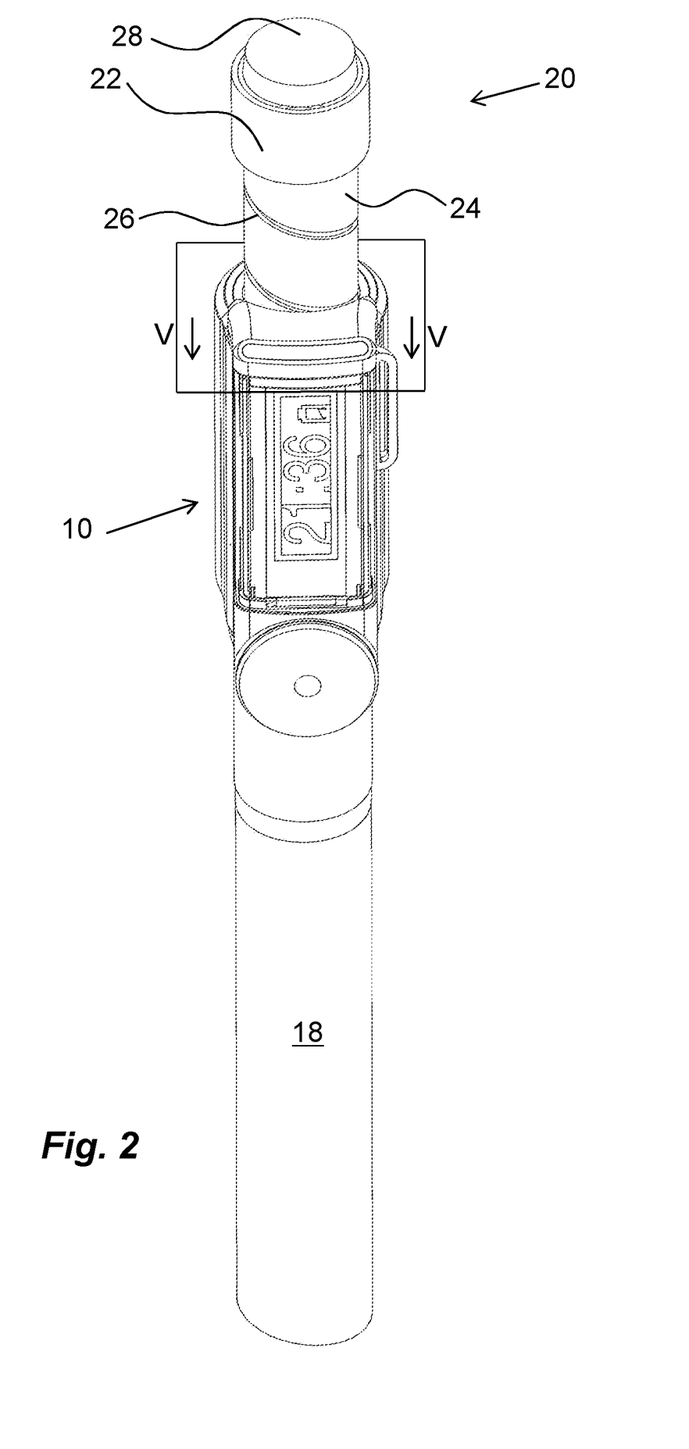
FIG. 2 shows a perspective view of a medicament delivery device with a monitoring unit attached.
Figure 3:
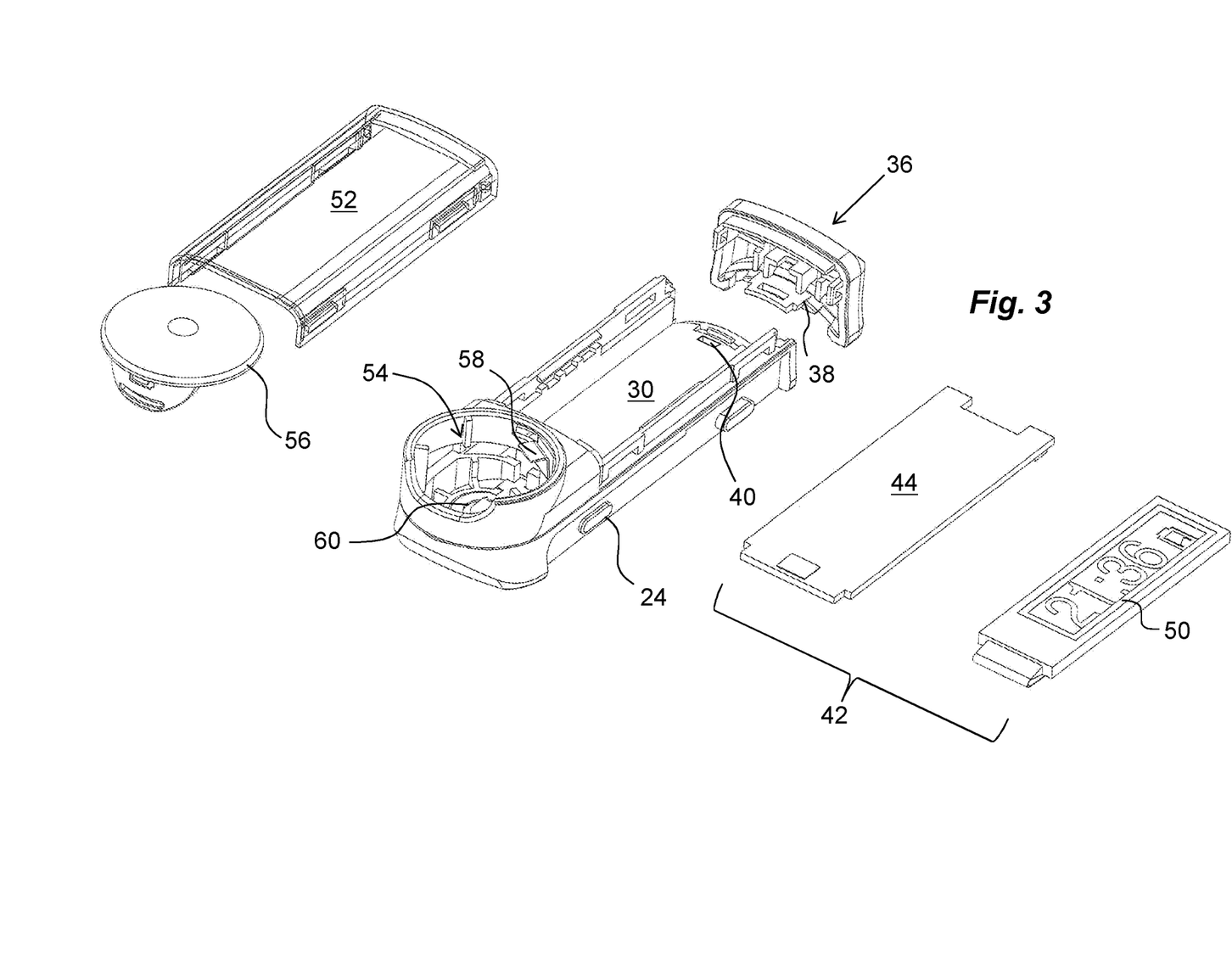
FIG. 3 shows an exploded view of the monitoring unit of FIG. 1.
Figure 4:
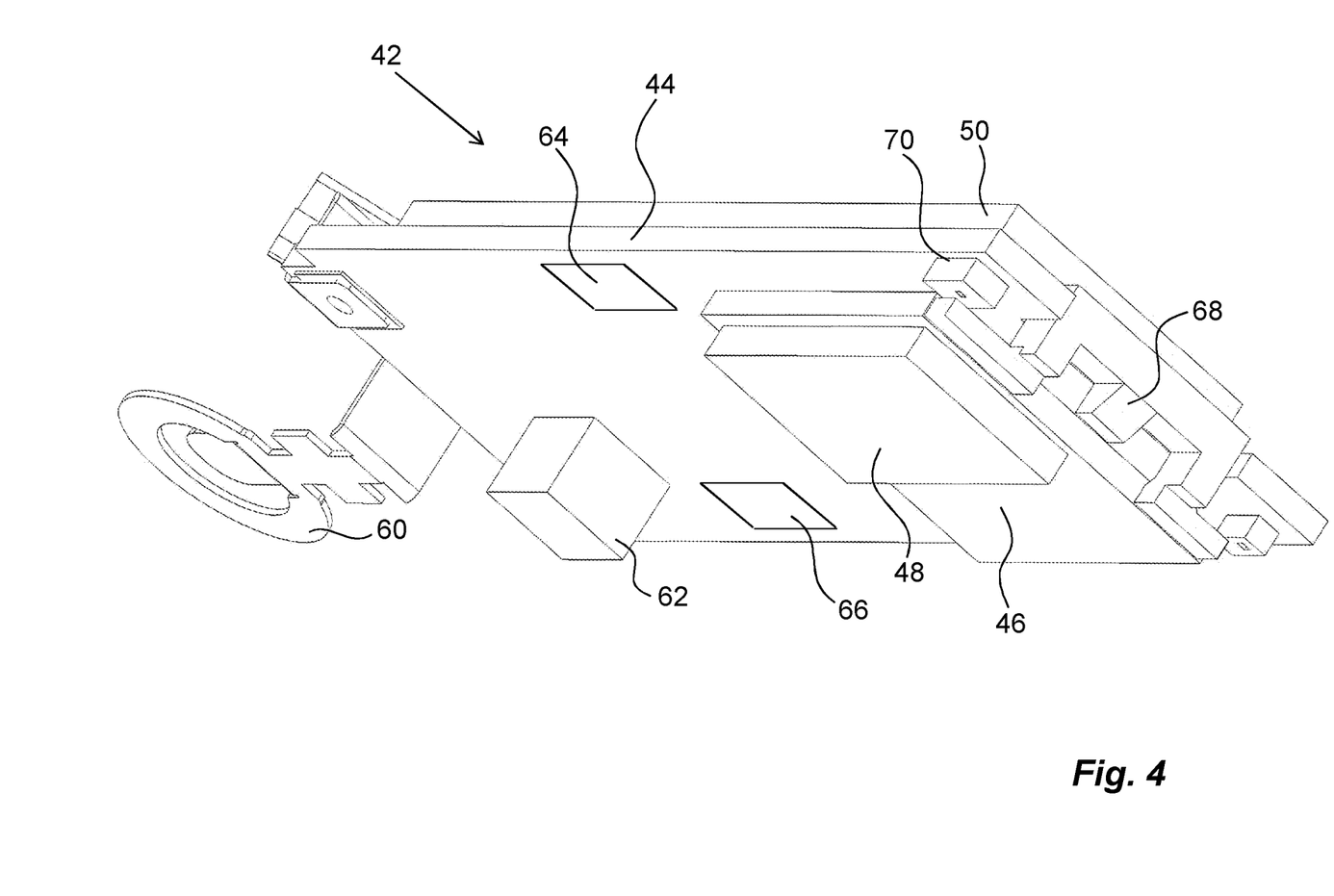
FIG. 4 shows a view in perspective from below of an electronic circuit of the monitoring unit of FIG. 1.
Figure 5:
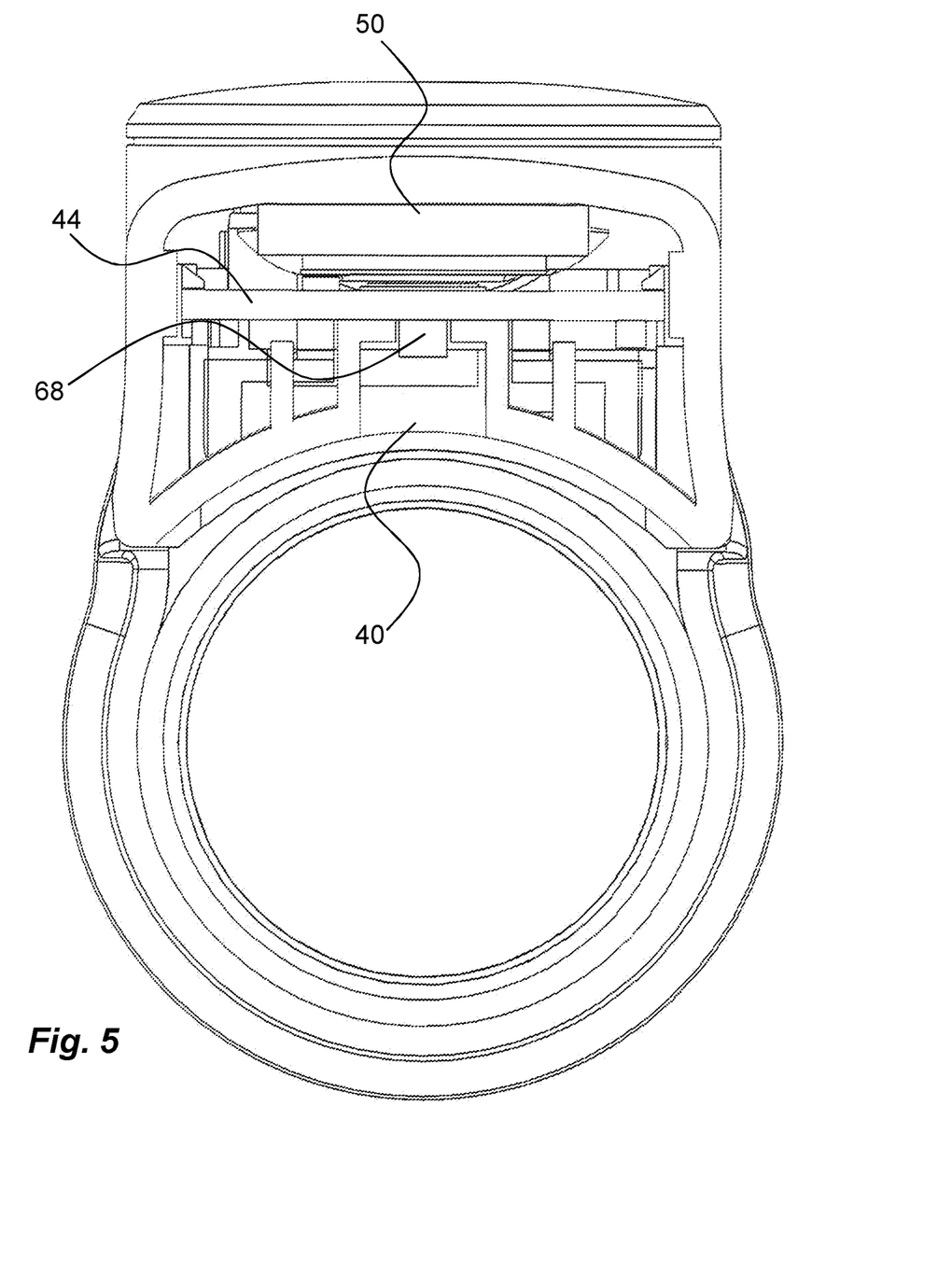
FIG. 5 shows a cross-sectional view through a plane V-V of FIG. 2.
Figure 6:
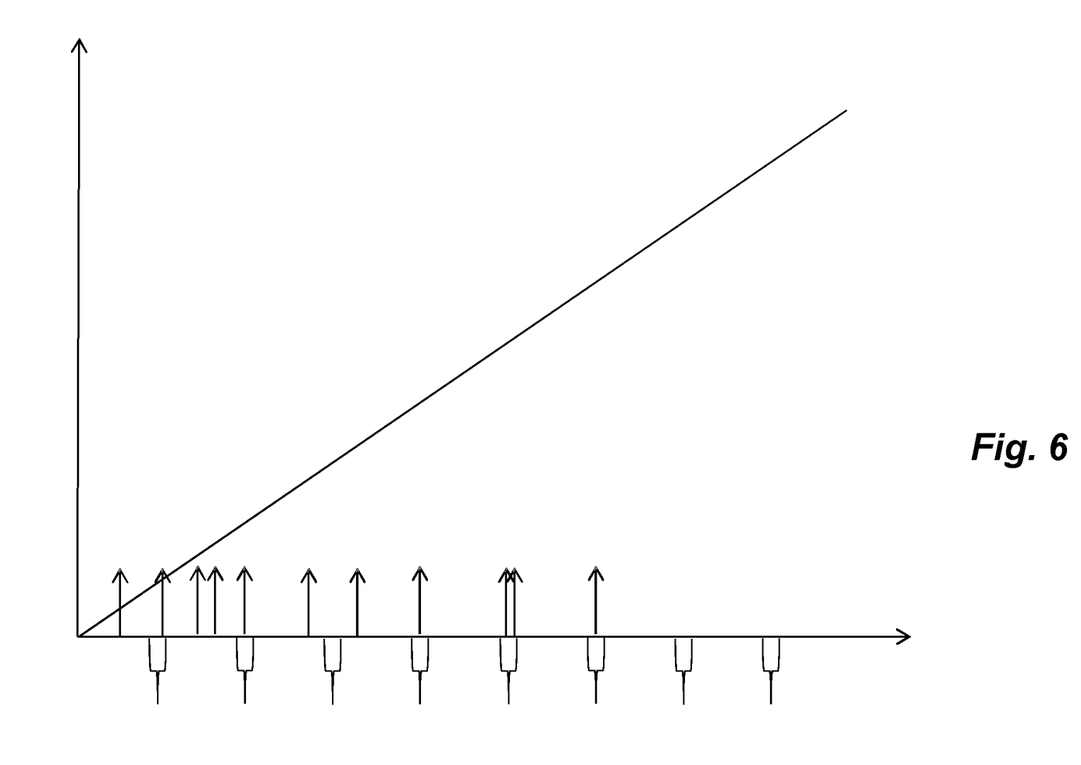
FIG. 6 shows a graph over click occurrences in relation to actual dose positions.

The monitoring unit 10 is further arranged with an electronic circuit 42, FIGS. 2 and 5. The electronic circuit 42 is preferably arranged on a printed circuit board 44 and is provided with a micro-controller unit 46 or MCU arranged to perform different functions based on program code. The electronic circuit 42 is further arranged with memory storage elements 48 in which the program code may be stored as well as data information obtained during operation of the monitoring unit 10. A user communication element in the form of a display 50, FIG. 2, is operationally connected to the electronic circuit 42, which display 50 is placed on an upper part of the housing 30 and is protected by a transparent cover 52. Apart from, and/or in addition to the display 50, the monitoring unit may be provided with further user communication elements such as LED-elements having e.g. different colours and/or flashing functions, vibrating elements, audio generating elements capable of creating sounds and even voice messages. The electronic circuit 42 is powered by a suitable power source that in the embodiment shown may be a button cell that is placed in an appropriate compartment 54 inside the housing. The button cell is held stationary by a removable lid 56. Suitable connecting leads 58, 60 are arranged between the electronics circuit and the poles of the button cell.

The electronic circuit 42 is preferably arranged with a communication module 62, FIG. 2, that is capable of transmitting and receiving data. Preferably the communication module 62 comprises modules for wireless communication with external devices. Preferably, but not exclusively, the modules for wireless communication use short-range wireless technologies such as for example ANT+, Bluetooth, NFC, RFID, Wi-Fi, Wireless HART, ZigBee, Z-wave, etc. At present, Bluetooth technology is preferred, being widely spread and included in many so called smart devices, but other communication technologies are naturally feasible. Further communication technologies may comprise cellular radio communication networks, e.g. GSM, 3G, 4G, etc. and/or wireless local area networks, which networks can provide access to the internet and thus to a large number of external data storage sources, data handling centres, etc.

The electronics circuit may further be arranged with different types of sensors operably capable of providing information regarding status of the monitoring unit. The sensors may include touch sensors 64 and temperature sensors 66 for instance. The touch sensor 64 may be designed such that if the medicament delivery device is picked up by a user in the low power mode, the touch sensor 64 detects that the medicament delivery device has been touched, which will cause the monitoring unit 10 to be activated. The temperature sensor 66 may be used for determining if a medicament delivery device has reached a temperature in which the medicament may be administered. This may for example be the case with medicament delivery devices having medicaments that require cool storage for preventing degradation but which medicaments need to be injected at room temperatures. The monitoring unit could then provide an indication to the user when the temperature has reached a level such that the medicament delivery device can be used.

A further sensor that can be used according to the invention is an optical sensor 68 capable of detecting movement of components of the medicament delivery device. One favourable solution is to use an optoelectronic sensor that can take successive images of a moving surface. Such a sensor does not require a specific surface or specific patterns in order to detect a movement of a component or element of a medicament delivery device. The optical sensor 68 is attached such on the electronic circuit 42 that when mounted in the housing 30, the optical sensor 68 is positioned in line with the passage 40 of the housing 30, FIG. 5.

Figure 7:
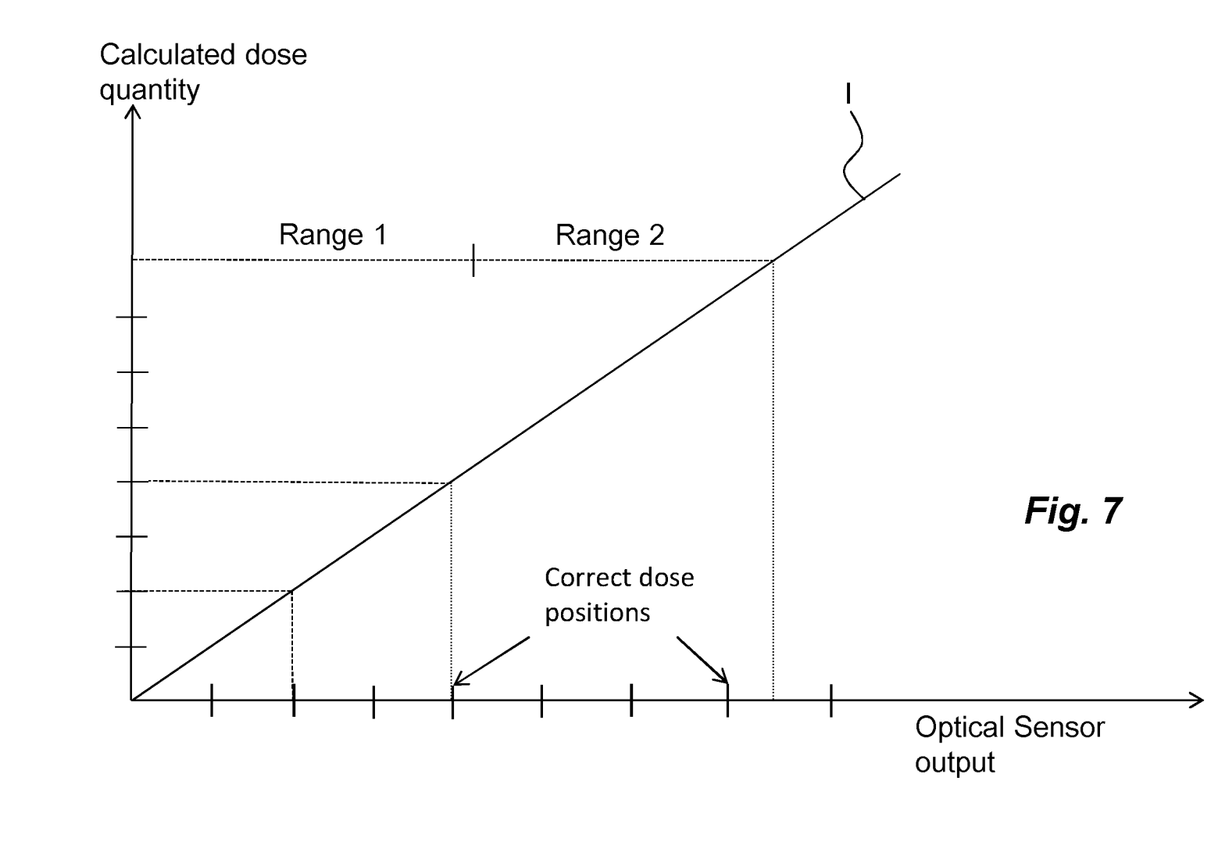
FIG. 7 shows a graph over the relation between optical sensor output and calculated dose quantity.

According to one feasible solution, the optical sensor is positioned adjacent the dose activation element 20. The position of the optical sensor 68 is such that it will not interfere with the mechanical operation of the dose activation element 20, neither when setting a dose nor when delivering a dose. Thus, the optical sensor 68 can detect the movement of the dose activation element and in particular the tubular extension 24, but this may not be sufficiently accurate in some occurrences, especially when the dose activating element is moved longer distances for setting larger doses. This is because the mechanical precision is not always so good whereby tolerance aspects start to play a role. As seen in FIG. 7, the moved distance of the dose activating element as measured by the optical sensor and obtained as output calculated doses is indicated on the X-axis and the calculated doses are indicated on the Y-axis. With a mechanism of the medicament delivery device without any deficiencies, a certain moved distance measured by the optical sensor should equate a correct dose position and thus correspond to a calculated dose in a linear correlation, line I. This is mostly true for shorter distances and thus for smaller doses, indicated by range 1, but for larger distances and thus larger doses, the inaccuracy of the constructions of the medicament delivery device and tolerance deviations result in a discrepancy between a correct dose position and the actual position as measured by the optical that should correspond to a calculated dose. Thus, as seen in FIG. 7, the measured distance that should correspond to a calculated dose do not correspond anymore and the user would be given a smaller dose than calculated.

Figure 8:
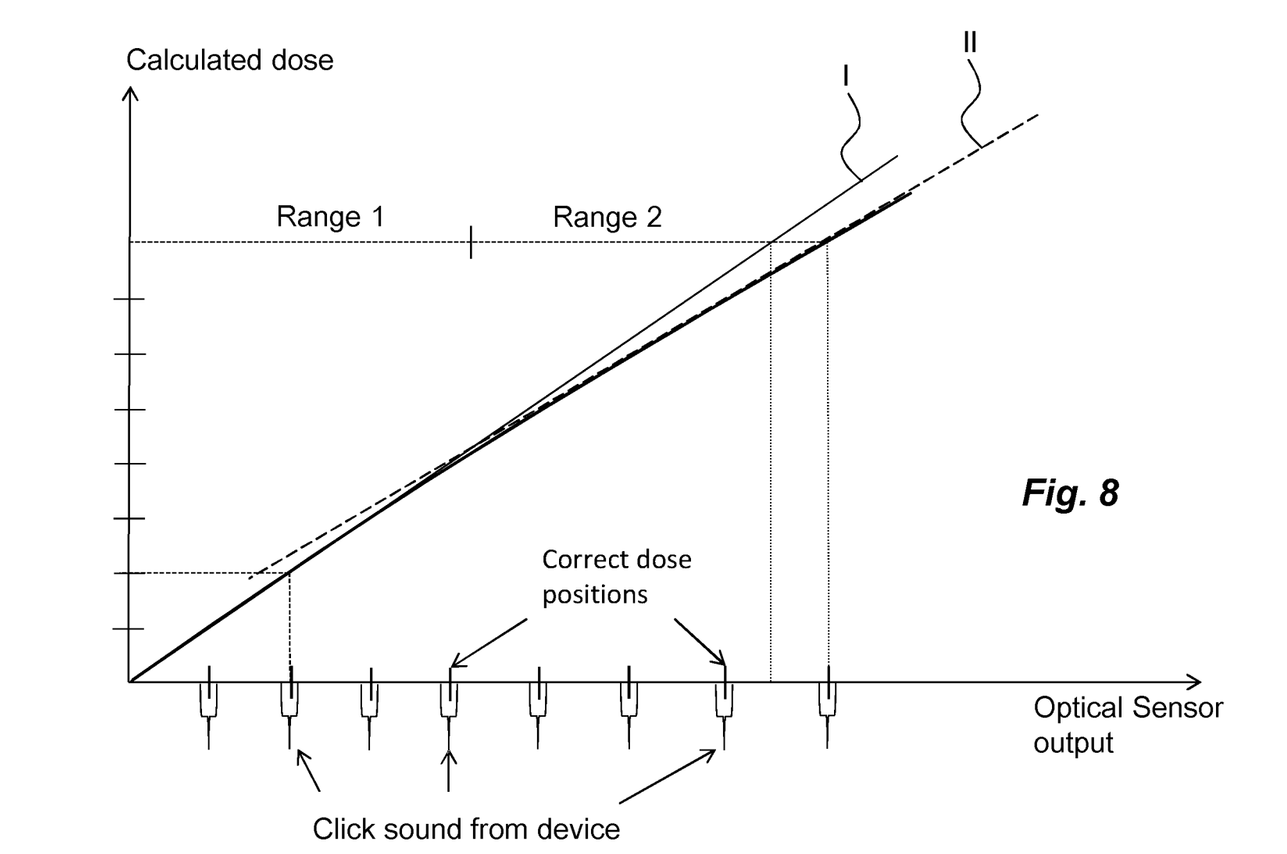
FIG. 8 shows the graph of FIG. 7 when compensation is made by also detecting and using click sound from device.

Therefore, according to a favourable solution, the electronic circuit 42 of the monitoring unit 10 is further arranged with an accelerometer 70 capable of measuring vibrations occurring in the medicament delivery device during especially the setting of a dose. Many medicament delivery devices are arranged with elements that produce specific clicks when a dose is set, where often each click corresponds to a dose unit. With the accelerometer 70, the clicks may be detected and recorded as a dose of medicament is set by the user turning the dose activating element. However, quite often the clicks produced are not exactly correlated to dose units, again due to tolerance issues, and further, clicks may be produced by other types of handling of the medicament delivery device than the setting of a dose. For instance, click sounds may occur when the medicament delivery device is tapped or dropped against a surface which may wrongly be interpreted as dose setting clicks. This is illustrated in FIG. 8 where the "forks" below the X-axis denote actual dose position with error range, and the arrows are detected tap events. If the two coincide, then a valid detection is performed. On the other hand, taps between the correct dose positions may provide erroneous detections. Also when several taps occur at a correct dose position, they might lead to erroneous or no detection.

In order to ensure a reliable and accurate detection of setting a dose unit, according to the invention, both movements and vibrations are detected. As seen from FIG. 8 the click sounds from the medicament delivery device are used to adjust the actual position of the dose activation element and thus the output from the optical sensor to a position where a click sound occurs, whereby the actual position of the dose activating element corresponds to the calculated dose quantity as seen in Range 2 in FIG. 8. Thus the use of two types of sensors provides the accuracy needed to detect when the correct dose has been set by the dose activation element.

The correlation between the optical sensor 68 and the accelerometer 70 thus provides the possibility of adjusting any deficiencies or discrepancies in the mechanical function of the medicament delivery device when setting a dose. The present invention may work with any medicament delivery device of the type where a dose is set and delivered by a dose activating element comprising some of the functions described above. Since most designs have their specific solutions regarding how the dose is set, such as thread pitch between the dose activating element and the housing of the medicament delivery device and how and when a dose click is produced, the monitoring unit according to the invention may be calibrated against a large number of different designs in order to function with a range of medicament delivery devices. In this regard, when the monitoring unit is to be used for a specific medicament delivery device for the first time, a setting mode may be entered and displayed on the monitoring unit, wherein the user choses the specific model among the range of medicament delivery devices that can be used with the monitoring unit. This step is then only necessary thereafter if the user changes the medicament delivery device. If he/she continues with the same device, the choosing step does not have to be repeated. In connection to this, there is a possibility that a calibrating step is performed for each medicament delivery device before the monitoring unit is used. This may for instance be relevant if there are significant differences in the mechanics between individual species of the same model of medicament delivery device. However, for most medicament delivery devices, this should not be necessary.

It is to be understood that the embodiment described above and shown in the drawings is to be regarded only as a non-limiting example and that the invention could be modified in many ways within the scope of the claims.

I claim:

1. A monitoring device arranged to be operably connected to a medicament delivery device including a manually operated movable dose activation element, the monitoring device comprising:
    a housing defining a passage, the passage having a first end configured to be positioned adjacent the medicament delivery device and a second end opposite the first end;
    an optical sensor configured to measure a movement of the dose activation element, wherein the optical sensor is positioned adjacent the second end of said passage and in line with the passage such that said optical sensor is spaced away from a surface of the dose activation element, and wherein the optical sensor is arranged to scan the surface of the dose activation element through the passage so as to detect a movement of said dose activation element from an initial position;
    an accelerometer configured to detect specific vibration spectra produced by the medicament delivery device when the dose activation element is operated; and
    an electronic circuit in communication with the optical sensor and the accelerometer, wherein the electronic circuit includes computing elements capable of correlating information from the optical sensor with information from the accelerometer when the dose activation element is operated in order to register when a correct dose has been set.

2. The monitoring device according to claim 1, wherein the specific vibration spectra is produced by the medicament delivery device at predetermined dose quantity intervals.

3. The monitoring device according to claim 2, wherein the accelerometer is arranged to detect and record audible clicks corresponding to the predetermined dose quantity intervals as a dose of medicament is set by a user turning the dose activation element.

4. The monitoring device according to claim 1, further comprising a user information interface capable of providing information to the user.

5. The monitoring device according to claim 4, wherein the user information interface comprises a display.

6. The monitoring device according to claim 1, further comprising a touch sensor.

7. The monitoring device according to claim 6, wherein the touch sensor is operably connected to the electronic circuit such that the electronic circuit is activated when the touch sensor detects a touch or movement of the monitoring device.

8. The monitoring device according to claim 1, further comprising a temperature sensor.

9. The monitoring device according to claim 8, wherein the temperature sensor is operably connected to the electronic circuit such that an indication is provided when a temperature detected by the temperature sensor has reached a certain level.

10. The monitoring device according to claim 1, further comprising at least one communication circuit designed and arranged to communicate with one or more external communication elements.

11. The monitoring device according to claim 10, wherein said communication circuit comprises near range communication technology.

12. The monitoring device according to claim 1, wherein correlating information from the optical sensor with information from the accelerometer when the dose activation element is operated comprises:
    measuring, via the optical sensor, a position of the dose activation element;
    detecting, via the accelerometer, an audible click corresponding to a predetermined dose quantity interval; and
    adjusting an actual position of the dose activation element and thus an output from the optical sensor to a position where the audible click occurs, whereby the actual position of the dose activation element corresponds to a calculated dose quantity.

13. A monitoring device arranged to be operably connected to a medicament delivery device including a manually operated movable dose activation element, the monitoring device comprising:
    an activation sensor configured to detect that the medicament delivery device has been moved by a user, wherein the activation sensor transitions the monitoring device from a low power mode to an activated mode in response to the detection that the medicament delivery device has been moved by the user;
    an optical sensor configured to measure a movement of the dose activation element, wherein the optical sensor is spaced away from a surface of the dose activation element, and wherein the optical sensor is arranged to scan the surface of the dose activation element so as to detect a movement of said dose activation element from an initial position;
    an accelerometer configured to detect specific vibration spectra produced by the medicament delivery device when the dose activation element is operated; and
    an electronic circuit in communication with the activation sensor, the optical sensor, and the accelerometer, wherein the electronic circuit includes computing elements capable of correlating information from the optical sensor with information from the accelerometer when the dose activation element is operated in order to register when a correct dose has been set.

14. The monitoring device of claim 13, wherein the activation sensor comprises a touch sensor.

15. The monitoring device of claim 13, wherein the specific vibration spectra is produced by the medicament delivery device at predetermined dose quantity intervals.

16. The monitoring device of claim 15, wherein the accelerometer is arranged to detect and record audible clicks corresponding to the predetermined dose quantity intervals as a dose of medicament is set by a user turning the dose activation element.

17. The monitoring device of claim 13, wherein correlating information from the optical sensor with information from the accelerometer when the dose activation element is operated comprises:
 measuring, via the optical sensor, a position of the dose activation element;
 detecting, via the accelerometer, an audible click corresponding to a predetermined dose quantity interval; and
 adjusting an actual position of the dose activation element and thus an output from the optical sensor to a position where the audible click occurs, whereby the actual position of the dose activation element corresponds to a calculated dose quantity.

18. A system for monitoring an operation of a medicament delivery device, the medicament delivery device comprising a manually operated movable dose activation element, the system comprising:
 a connecting element arranged with a first fixation element configured to removably connect to a support surface of the medicament delivery device; and
 a monitoring unit arranged with a housing defining a passage and an attachment element, wherein the attachment element is configured to interact with a second fixation element of the connecting element, and
 wherein the passage includes a first end configured to be positioned adjacent said medicament delivery device and a second end opposite the first end,
 wherein the monitoring unit includes an optical sensor configured to measure a movement of the dose activation element, wherein the optical sensor is positioned adjacent the second end of said passage and in line with the passage such that said optical sensor is spaced away from a surface of the dose activation element, and wherein the optical sensor is arranged to scan the surface of the dose activation element through the passage so as to detect a movement of said dose activation element from an initial position,
 wherein the monitoring unit includes an accelerometer configured to detect specific vibration spectra produced by the medicament delivery device when the dose activation element is operated, and
 wherein the monitoring unit includes an electronic circuit in communication with the optical sensor and the accelerometer, wherein the electronic circuit includes computing elements capable of correlating information from the optical sensor with information from the accelerometer when the dose activation element is operated in order to register when a correct dose has been set.

19. The system according to claim 18, wherein the connecting element is an annular sleeve.

20. The system according to claim 18, wherein the manually operated movable dose activation element further comprises a tubular extension, and wherein the optical sensor is configured to detect the movement of said tubular extension.

* * * * *